(12) United States Patent
Suzuki et al.

(10) Patent No.: US 11,981,763 B2
(45) Date of Patent: May 14, 2024

(54) RESIN COMPOSITION FOR STEREOLITHOGRAPHIC MODELING

(71) Applicant: KURARAY NORITAKE DENTAL INC., Kurashiki (JP)

(72) Inventors: Kenji Suzuki, Niigata (JP); Misaki Ito, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 124 days.

(21) Appl. No.: 17/612,862

(22) PCT Filed: May 21, 2020

(86) PCT No.: PCT/JP2020/020096
§ 371 (c)(1),
(2) Date: Nov. 19, 2021

(87) PCT Pub. No.: WO2020/235628
PCT Pub. Date: Nov. 26, 2020

(65) Prior Publication Data
US 2022/0251275 A1 Aug. 11, 2022

(30) Foreign Application Priority Data
May 21, 2019 (JP) ................. 2019-095520

(51) Int. Cl.
| | | |
|---|---|---|
| C08F 2/46 | (2006.01) |
| B29C 64/124 | (2017.01) |
| B33Y 10/00 | (2015.01) |
| B33Y 70/00 | (2020.01) |
| C08F 2/50 | (2006.01) |
| C08F 265/06 | (2006.01) |
| C08G 61/04 | (2006.01) |
| C08K 3/36 | (2006.01) |
| C08K 5/14 | (2006.01) |
| C08K 5/54 | (2006.01) |
| C08K 9/06 | (2006.01) |
| B29K 105/00 | (2006.01) |
| B29K 105/16 | (2006.01) |

(52) U.S. Cl.
CPC .......... C08F 265/06 (2013.01); B29C 64/124 (2017.08); B33Y 10/00 (2014.12); B33Y 70/00 (2014.12); C08K 3/36 (2013.01); C08K 5/14 (2013.01); C08K 5/5406 (2013.01); C08K 9/06 (2013.01); *B29K 2105/0002* (2013.01); *B29K 2105/16* (2013.01)

(58) Field of Classification Search
CPC .. B29C 64/124; C08G 18/672; C08G 18/755; C08G 18/4298; C08G 18/44; C08G 18/42; C08F 2/50; C08F 222/1025; C08F 222/102; C08F 220/58; C08F 220/1811; A61K 6/62; A61K 6/76; A61K 6/887; B29K 2105/0002; B29K 2105/16; A61C 13/0013; B33Y 70/00; B33Y 410/00; C08K 3/36; C08K 9/06; C08K 5/5406; C08L 33/08; C08L 33/10; C08L 33/26
USPC ........................ 522/6, 71, 1, 189, 184; 520/1
See application file for complete search history.

(56) References Cited

U.S. PATENT DOCUMENTS

2017/0014312 A1  1/2017 Suzuki

FOREIGN PATENT DOCUMENTS

| CN | 108912287 A | | 11/2018 |
|---|---|---|---|
| CN | 109232831 | * | 1/2019 |
| CN | 109232831 A | | 1/2019 |
| EP | 3960123 | * | 3/2022 |
| JP | 56-144478 A | | 11/1981 |
| JP | 60-247515 A | | 12/1985 |
| JP | 8-300492 A | | 11/1996 |
| JP | 9-3109 A | | 1/1997 |
| JP | 10-245525 A | | 9/1998 |
| JP | 2000-159621 A | | 6/2000 |
| JP | 2005-170813 A | | 6/2005 |
| JP | 2011-225526 A | | 11/2011 |
| JP | 2011225526 | * | 11/2011 |

(Continued)

OTHER PUBLICATIONS

Kawana et al, JP 2011225526 Machine translation, Nov. 10, 2011 (Year: 2011).*

(Continued)

*Primary Examiner* — Jessica Whiteley
(74) *Attorney, Agent, or Firm* — Oblon, McClelland, Maier & Neustadt, L.L.P.

(57) ABSTRACT

The present invention provides a resin composition for stereolithographic modeling emitting a weak odor, having desirable shape accuracy, and made into a cured product having desirable strength, toughness, and color tone when used for stereolithographic modeling. The present invention relates to a resin composition for stereolithographic modeling, comprising: a polymerizable monomer (A); a photopolymerization initiator (B), and an organic peroxide (C), wherein the polymerizable monomer (A) comprises a (meth) acrylic acid ester compound (A-1) having a viscosity of 1,000 mPa·s or less and a normal boiling point of 270° C. or more and/or a (meth)acrylamide compound (A-2) having a viscosity of 1,000 mPa·s or less and a normal boiling point of 200° C. or more, and the photopolymerization initiator (B) is at least one selected from a (bis)acylphosphine oxide, an α-hydroxyketone compound, an α-aminoketone compound, a benzoin alkyl ether compound, a thioxanthone, a ketal, an α-diketone, and an anthraquinone.

12 Claims, No Drawings

(56) References Cited

FOREIGN PATENT DOCUMENTS

| | | | |
|---|---|---|---|
| JP | 2016-98202 A | | 5/2016 |
| JP | 2016098202 | * | 5/2016 |
| JP | 2017-43652 A | | 3/2017 |
| JP | 2018-193342 A | | 12/2018 |
| JP | 2018193342 | * | 12/2018 |
| WO | WO 2015/129180 A1 | | 9/2015 |
| WO | WO 2018/038056 A1 | | 3/2018 |

OTHER PUBLICATIONS

Suzuki, JP 2016098202 Machine Translation, May 30, 2016 (Year: 2016).*
Kita et al, JP 2018-193342 Machine Translation, Dec. 6, 2018 (Year: 2018).*
Song et al, CN 109232831 Machine Translation, Jan. 18, 2019 (Year: 2019).*
Extended European Search Report dated May 16, 2023, in corresponding European Patent Application No. 20810600.5, 12 pages.
International Search Report dated Aug. 11, 2020 in PCT/JP2020/020096 filed May 21, 2020, 3 pages.

* cited by examiner

RESIN COMPOSITION FOR STEREOLITHOGRAPHIC MODELING

TECHNICAL FIELD

The present invention relates to a resin composition for stereolithographic modeling and a method for producing a three-dimensional object with the resin composition for stereolithographic modeling. Specifically, according to the present invention, a three-dimensional object emitting a weak odor, having desirable shape accuracy, and having desirable strength, toughness, and color tone can be obtained by stereolithographical fabrication. The present invention relates to a resin composition for stereolithographic modeling particularly suited for a dental material and a method for optically producing a three-dimensional object with the resin composition for stereolithographic modeling.

BACKGROUND ART

Patent Literature 1 discloses stereolithographic modeling in which a three-dimensional object is produced through repeated exposure of controlled, necessary amounts of light energy to a liquid photocurable resin to cure the resin layer-by-layer as it is supplied onto the previously cured layer. Patent Literature 2 proposes a basic method for practical application of this technique, and, since its proposal, many other stereolithographic modeling techniques have been proposed.

A technique commonly used for optical fabrication of a three-dimensional object is as follows. A computer-controlled ultraviolet laser is selectively applied to draw a desired pattern on the surface of a liquid photocurable resin composition placed in a vat. The resin is cured at a predetermined thickness, and another cured layer is continuously formed on the cured layer by applying an ultraviolet laser to the liquid photocurable resin composition supplied onto the previously cured layer in an amount necessary to form a single layer. The layering process is repeated to produce a three-dimensional object of a desired shape. This technique has attracted great interest because it enables easy production of a desired three-dimensional object in a relatively short time period, even when the object has a very complex shape.

Three-dimensional objects produced by stereolithography are used in an increasingly wider range of applications, from simple concept models to more complex models such as test models and prototypes. This has created a demand for higher shape accuracy in these three-dimensional objects. In addition to satisfying such properties, these products are also required to have high mechanical properties. The field of dental materials is thought to greatly benefit from stereolithography because dental prostheses such as crowns, bridges, denture bases, and dental mouthpieces require shapes that vary from patient to patient, aside from being complex in shape. However, required shape accuracy (conformity) is extremely high and, moreover, strength enough to endure biting and aesthetics are also required.

Against this background, various techniques are proposed that are intended to enable stereolithographic modeling with high shape accuracy. For example, Patent Literature 3 proposes a resin composition for stereolithographic modeling including a metallocene compound and an organic peroxide. Patent Literature 4 proposes a resin composition for stereolithographic modeling including a particular urethanized (meth)acrylic compound and a particular acrylamide compound and having, for example, high shape accuracy and high fracture resistance.

CITATION LIST

Patent Literature

Patent Literature 1: JP S56(1981)-144478 A
Patent Literature 2: JP S60(1985)-247515 A
Patent Literature 3: JP H8(1996)-300492 A
Patent Literature 4: WO 2018/038056

SUMMARY OF INVENTION

Technical Problem

However, Patent Literature 3 does not specifically describe mechanical properties of the resin composition for stereolithographic modeling. A polymerizable monomer included therein has a significantly strong odor, which makes the resin composition disadvantageous in practical use. Moreover, there is no description about a color tone although the metallocene compound included as a photopolymerization initiator may affect a color tone of a cured product because of strong absorption at 450 nm or more in the visible region. On the other hand, the resin composition for stereolithographic modeling of Patent Literature 4, which is suited as a soft material for, for example, mouthguards because of its high flexibility, needs to be improved from the perspective of practical use as a dental material, for example, a dental prosthesis which needs to have strength and toughness, such as a crown or a bridge. Moreover, although coloring of a cured product due to the acrylamide compound is another possible problem, there is no description about color tone.

It is accordingly an object of the present invention to provide a resin composition for stereolithographic modeling that emits a weak odor, has desirable shape accuracy, and is made into a cured product having desirable strength, toughness, and color tone when used for stereolithographical fabrication.

Solution to Problem

As a result of intensive studies for achieving the above object, the present inventors found that a resin composition for stereolithographic modeling that emits a weak odor and has desirable shape accuracy can be obtained with the use of a (meth)acrylic acid ester compound having a viscosity of a particular value or less and a normal boiling point of a particular value or more and/or a (meth)acrylamide compound having a viscosity of a particular value or less and a normal boiling point of a particular value or more as a polymerizable monomer(s). The present inventors also found that intentional inclusion of an organic peroxide, which generally tends to be avoided for fear of reaction with an amine compound such as an acrylamide compound during storage of resin compositions for stereolithographic modeling, in combination with a specific photopolymerization initiator results in a cured product having desirable strength and toughness and improved color tone. Through further studies based on these findings, the present inventors have completed the present invention.

Specifically, the present invention includes the following aspects.

[1] A resin composition for stereolithographic modeling, comprising:
a polymerizable monomer (A);
a photopolymerization initiator (B), and
an organic peroxide (C), wherein
the polymerizable monomer (A) comprises a (meth)acrylic acid ester compound (A-1) having a viscosity of 1,000 mPa·s or less and a normal boiling point of 270° C. or more and/or a (meth)acrylamide compound (A-2) having a viscosity of 1,000 mPa·s or less and a normal boiling point of 200° C. or more, and
the photopolymerization initiator (B) is at least one selected from a (bis)acylphosphine oxide, an α-hydroxyketone compound, an α-aminoketone compound, a benzoin alkyl ether compound, a thioxanthone, a ketal, an α-diketone, and an anthraquinone.

[2] The resin composition for stereolithographic modeling according to [1], wherein the polymerizable monomer (A) further comprises a polyfunctional (meth)acrylic acid ester compound (A-3) having a viscosity of more than 1,000 mPa·s.

[3] The resin composition for stereolithographic modeling according to [2], wherein the polyfunctional (meth)acrylic acid ester compound (A-3) has a urethane bond per molecule.

[4] The resin composition for stereolithographic modeling according to [3], wherein the polyfunctional (meth)acrylic acid ester compound (A-3) has at least one structure selected from the group consisting of a polyester, a polycarbonate, a polyurethane, a polyether, a poly(conjugated diene), and a hydrogenated poly(conjugated diene).

[5] The resin composition for stereolithographic modeling according to any one of [1] to [4], wherein the organic peroxide (C) is at least one selected from a ketone peroxide, a hydroperoxide, a diacyl peroxide, a dialkyl peroxide, a peroxyketal, a peroxyester, and a peroxydicarbonate.

[6] The resin composition for stereolithographic modeling according to any one of [1] to [5], wherein
the polymerizable monomer (A) comprises the (meth)acrylic acid ester compound (A-1) having a viscosity of 1,000 mPa·s or less and a normal boiling point of 270° C. or more, and
the (meth)acrylic acid ester compound (A-1) comprises a monofunctional (meth)acrylic acid ester compound having an aromatic ring and/or a monofunctional (meth)acrylic acid ester compound having an alicyclic ring.

[7] The resin composition for stereolithographic modeling according to [6], wherein the (meth)acrylic acid ester compound (A-1) comprises a monofunctional (meth)acrylic acid ester compound having an alicyclic ring.

[8] The resin composition for stereolithographic modeling according to [7], wherein the monofunctional (meth)acrylic acid ester compound having an alicyclic ring is a monofunctional (meth)acrylic acid ester compound having a polyalicyclic ring.

[9] The resin composition for stereolithographic modeling according to any one of [1] to [8], further comprising a filler (D).

[10] The resin composition for stereolithographic modeling according to [9], wherein an average primary particle diameter of the filler (D) is 1.0 μm or less.

[11] A dental material comprising a cured product of the resin composition for stereolithographic modeling according to any one of [1] to [10].

[12] A method for producing a three-dimensional object with the resin composition for stereolithographic modeling according to any one of [1] to [10] by stereolithographic modeling.

Advantageous Effects of Invention

The resin composition for stereolithographic modeling of the present invention emits a weak odor, has desirable shape accuracy, and is made into a cured product having desirable strength, toughness, and color tone when used for stereolithographical fabrication. Therefore, the resin composition for stereolithographic modeling of the present invention can be suitably used as a dental material (for example, a dental prosthesis).

DESCRIPTION OF EMBODIMENTS

The resin composition for stereolithographic modeling of the present invention comprises a polymerizable monomer (A), a photopolymerization initiator (B), and an organic peroxide (C). The polymerizable monomer (A) comprises a (meth)acrylic acid ester compound (A-1) having a viscosity of 1,000 mPa·s or less and a normal boiling point of 270° C. or more and/or a (meth)acrylamide compound (A-2) having a viscosity of 1,000 mPa·s or less and a normal boiling point of 200° C. or more. The photopolymerization initiator (B) includes at least one selected from a (bis)acylphosphine oxide, an α-hydroxyketone compound, an α-aminoketone compound, a benzoin alkyl ether compound, a thioxanthone, a ketal, an α-diketone, and an anthraquinone. In the present specification, the upper limits and lower limits of numeric ranges (for example, ranges of contents of components, ranges of values calculated from components, and numeric ranges of physical properties) can be combined appropriately.

Polymerizable Monomer (A)

The polymerizable monomer (A) comprises the (meth)acrylic acid ester compound (A-1) having a viscosity of 1,000 mPa·s or less and a normal boiling point of 270° C. or more and/or the (meth)acrylamide compound (A-2) having a viscosity of 1,000 mPa·s or less and a normal boiling point of 200° C. or more.

Specific examples of the polymerizable monomer (A) used in the resin composition for stereolithographic modeling of the present invention include esters such as a (meth)acrylic acid ester compound, a (meth)acrylamide compound, α-cyanoacrylic acid, (meth)acrylic acid, α-halogenated acrylic acid, crotonic acid, sorbic acid, maleic acid, and itaconic acid. The term "(meth)acryl" as used in the present specification collectively refers to "methacryl" and "acryl". The term "(meth)acrylate" collectively refers to "acrylic acid ester" and "methacrylic acid ester".

As used herein, "viscosity" is a viscosity measured with a Brookfield viscometer at 25° C. Measurement conditions such as time and rotational speed are appropriately adjusted according to viscosity. As used herein, "normal boiling point" is a measured value by atmospheric distillation. For compounds for which normal boiling points are not observable, a measured value of boiling point at reduced pressure by vacuum distillation is converted into a normal boiling point using a boiling point vs. pressure chart (The Science of Petroeum, Vol. II. p. 1281 (1938)).

(Meth)Acrylic Acid Ester Compound (A-1) Having a Viscosity of 1,000 mPa·s or Less and a Normal Boiling Point of 270° C. or More In the resin composition for stereolithographic modeling of the present invention, the (meth)acrylic acid ester compound (A-1) having a viscosity of 1,000 mPa·s or less and a normal boiling point of 270° C. or more (hereinafter, also referred to simply as "(meth)acrylic acid ester compound (A-1)") is used to lower the viscosity of the resin composition for stereolithographic modeling without producing an odor and obtain desirable shape accuracy. The (meth)acrylic acid ester compound (A-1) is also used to impart strength and toughness to a cured product of the resin composition for stereolithographic modeling. With a normal boiling point of 270° C. or more, the resin composition for stereolithographic modeling of the present invention is less likely to produce an unpleasant odor. The normal boiling point of the (meth)acrylic acid ester compound (A-1) is preferably 280° C. or more, more preferably 285° C. or more. The normal boiling point of the (meth)acrylic acid ester compound (A-1) is preferably 450° C. or less, more preferably 400° C. or less. The viscosity of the (meth)acrylic acid ester compound (A-1) is preferably 750 mPa·s or less, more preferably 500 mPa·s or less. The (meth)acrylic acid ester compound (A-1) may be used alone, or two or more thereof may be used in combination.

Examples of the (meth)acrylic acid ester compound (A-1) in the present invention include monofunctional (meth)acrylic acid ester compounds having one (meth)acryloyl group, and polyfunctional (meth)acrylic acid ester compounds having a plurality of (meth)acryloyl groups. In view of obtaining a cured product having improved toughness, monofunctional (meth)acrylic acid ester compounds are more preferred. Preferably, the (meth)acrylic acid ester compound (A-1) does not contain a urethane bond.

Examples of the monofunctional (meth)acrylic acid ester compounds include an aliphatic monofunctional (meth)acrylic acid ester compound having an aliphatic hydrocarbon group and a monofunctional (meth)acrylic acid ester compound having a ring structure. Examples of the monofunctional (meth)acrylic acid ester compound having a ring structure include a monofunctional (meth)acrylic acid ester compound having an aromatic ring, a monofunctional (meth)acrylic acid ester compound having an alicyclic ring, and a monofunctional (meth)acrylic acid ester compound having a heterocycle. The number of rings included in the ring structure may be one or may be two or more. Examples of the aliphatic monofunctional (meth)acrylic acid ester compound having an aliphatic hydrocarbon group include aliphatic monofunctional (meth)acrylic acid ester compounds such as lauryl (meth)acrylate, tridecyl (meth)acrylate, tetradecyl (meth)acrylate, pentadecyl (meth)acrylate, cetyl (meth)acrylate, oleyl (meth)acrylate, isostearyl (meth)acrylate, 4-hydroxybutyl (meth)acrylate, 6-hydroxyhexyl (meth)acrylate, 10-hydroxydecyl (meth)acrylate, glycerol mono(meth)acrylate, and erythritol mono(meth)acrylate. In the aliphatic hydrocarbon group, the number of carbon atoms is preferably 1 to 30, more preferably 2 to 25, even more preferably 3 to 20. Examples of the monofunctional (meth)acrylic acid ester compound having an aromatic ring include monofunctional (meth)acrylic acid ester compounds having two or more aromatic rings, such as o-phenylphenol (meth)acrylate, m-phenylphenol (meth)acrylate, p-phenylphenol (meth)acrylate, methoxylated-o-phenylphenol (meth)acrylate, methoxylated-m-phenylphenol (meth)acrylate, methoxylated-p-phenylphenol (meth)acrylate, ethoxylated-o-phenylphenol (meth)acrylate, ethoxylated-m-phenylphenol (meth)acrylate, ethoxylated-p-phenylphenol (meth)acrylate, propoxylated-o-phenylphenol (meth)acrylate, propoxylated-m-phenylphenol (meth)acrylate, propoxylated-p-phenylphenol (meth)acrylate, butoxylated-o-phenylphenol (meth)acrylate, butoxylated-m-phenylphenol (meth)acrylate, butoxylated-p-phenylphenol (meth)acrylate, o-phenoxybenzyl (meth)acrylate, m-phenoxybenzyl (meth)acrylate, p-phenoxybenzyl (meth)acrylate, 2-(o-phenoxyphenyl)ethyl (meth)acrylate, 2-(m-phenoxyphenyl)ethyl (meth)acrylate, 2-(p-phenoxyphenyl)ethyl (meth)acrylate, 3-(o-phenoxyphenyl)propyl (meth)acrylate, 3-(m-phenoxyphenyl)propyl (meth)acrylate, 3-(p-phenoxyphenyl)propyl (meth)acrylate, 4-(o-phenoxyphenyl)butyl (meth)acrylate, 4-(m-phenoxyphenyl)butyl (meth)acrylate, 4-(p-phenoxyphenyl)butyl (meth)acrylate, 5-(o-phenoxyphenyl)pentyl (meth)acrylate, 5-(m-phenoxyphenyl)pentyl (meth)acrylate, 5-(p-phenoxyphenyl)pentyl (meth)acrylate, 6-(o-phenoxyphenyl)hexyl (meth)acrylate, 6-(m-phenoxyphenyl)hexyl (meth)acrylate, and 6-(p-phenoxyphenyl)hexyl (meth)acrylate. Examples of the monofunctional (meth)acrylic acid ester compound having an alicyclic ring include: monofunctional (meth)acrylic acid ester compound having a monoalicyclic ring, such as 1,4-cyclohexanedimethanol (meth)acrylate; and monofunctional (meth)acrylic acid ester compounds having a polyalicyclic ring, such as 1-adamantyl (meth)acrylate, 2-adamantyl (meth)acrylate, 2-methyl-2-adamantyl (meth)acrylate, 2-ethyl-2-adamantyl (meth)acrylate, 3-hydroxy-1-adamantyl (meth)acrylate, and dicyclopentanyl (meth)acrylate. Examples of the monofunctional (meth)acrylic acid ester compound having a heterocycle include: monofunctional (meth)acrylic acid ester compounds having a heterocycle containing only a nitrogen atom as a hetero atom; monofunctional (meth)acrylic acid ester compounds having a heterocycle containing a nitrogen atom and a sulfur atom and/or an oxygen atom as hetero atoms; monofunctional (meth)acrylic acid ester compounds having a heterocycle containing only a sulfur atom as a hetero atom; monofunctional (meth)acrylic acid ester compounds having a heterocycle containing only an oxygen atom as a hetero atom; and monofunctional (meth)acrylic acid ester compound having a heterocycle containing a sulfur atom and an oxygen atom as hetero atoms. In view of improving the viscosity of the resin composition for stereolithographic modeling and the toughness of a cured product, the monofunctional (meth)acrylic acid ester compounds are more preferably lauryl (meth)acrylate, tridecyl (meth)acrylate, o-phenylphenol (meth)acrylate, m-phenylphenol (meth)acrylate, p-phenylphenol (meth)acrylate, methoxylated-o-phenylphenol (meth)acrylate, o-phenoxybenzyl (meth)acrylate, m-phenoxybenzyl (meth)acrylate, p-phenoxybenzyl (meth)acrylate, and dicyclopentanyl (meth)acrylate, even more preferably lauryl (meth)acrylate, tridecyl (meth)acrylate, tetradecyl (meth)acrylate, pentadecyl (meth)acrylate, cetyl (meth)acrylate, oleyl (meth)acrylate, and dicyclopentanyl (meth)acrylate, particularly preferably lauryl (meth)acrylate, tridecyl (meth)acrylate, tetradecyl (meth)acrylate, m-phenoxybenzyl (meth)acrylate, and dicyclopentanyl (meth)acrylate, most preferably lauryl (meth)acrylate, m-phenoxybenzyl (meth)acrylate, and dicyclopentanyl (meth)acrylate.

Examples of the polyfunctional (meth)acrylic acid ester compounds include aromatic bifunctional (meth)acrylic acid ester compounds, aliphatic bifunctional (meth)acrylic acid ester compounds, and tri- and higher-functional (meth)acrylic acid ester compounds.

Examples of the aromatic bifunctional (meth)acrylic acid ester compounds include 2,2-bis(4-(meth)acryloyloxypolyethoxyphenyl)propane, 2,2-bis(4-(meth)acryloyloxytetraethoxyphenyl)propane, and 2,2-bis(4-(meth)acryloyloxypentaethoxyphenyl)propane.

Examples of the aliphatic bifunctional (meth)acrylic acid ester compounds include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, and 1,2-bis(3-methacryloyloxy-2-hydroxypropoxy)ethane.

Examples of the tri- and higher-functional (meth)acrylic acid ester compounds include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, and dipentaerythritol penta(meth)acrylate.

The resin composition for stereolithographic modeling of the present invention comprises preferably 1.0 to 80 mass % of (meth)acrylic acid ester compound (A-1) in the total amount of the polymerizable monomer (A). In view of improving fabricability and providing a cured product having improved strength and toughness, the content of (meth)acrylic acid ester compound (A-1) is more preferably 5 to 70 mass %, even more preferably 10 to 60 mass %.

(Meth)Acrylamide Compound (A-2) Having a Viscosity of 1,000 mPa·s or Less and a Normal Boiling Point of 200° C. or More In the resin composition for stereolithographic modeling of the present invention, the (meth)acrylamide compound (A-2) having a viscosity of 1,000 mPa·s or less and a normal boiling point of 200° C. or more (hereinafter, also referred to simply as "(meth)acrylamide compound (A-2)") is used to lower the viscosity of the resin composition for stereolithographic modeling without producing an odor and obtain desirable shape accuracy. The (meth)acrylamide compound (A-2) is also used to impart strength and toughness to a cured product of the resin composition for stereolithographic modeling. With a normal boiling point of 200° C. or more, the resin composition for stereolithographic modeling of the present invention is less likely to produce an unpleasant odor. The normal boiling point of (meth)acrylamide compound (A-2) is preferably 220° C. or more, more preferably 240° C. or more. The normal boiling point of the (meth)acrylamide compound (A-2) is not particularly limited, and is 400° C. or less, more preferably 350° C. or less. The viscosity of the (meth)acrylamide compound (A-2) is 750 mPa·s or less, more preferably 500 mPa·s or less. The (meth)acrylamide compound (A-2) may be used alone, or two or more thereof may be used in combination.

Examples of the (meth)acrylamide compound (A-2) in the present invention include: monofunctional (meth)acrylamide compounds having no amino group, such as N,N-dimethyl(meth)acrylamide, N,N-diethyl(meth)acrylamide, N,N-di-n-propyl(meth)acrylamide, N-isopropyl(meth)acrylamide, N-t-butyl(meth)acrylamide, N-t-octylacrylamide, N,N-di-n-butyl(meth)acrylamide, N,N-di-n-hexyl(meth)acrylamide, N,N-di-n-octyl(meth)acrylamide, N,N-di-2-ethylhexyl(meth)acrylamide, N-(2-hydroxyethyl)(meth)acrylamide, N,N-bis(2-hydroxyethyl)(meth)acrylamide, N-acryloylmorpholine; and monofunctional (meth)acrylamide compounds such as monofunctional (meth)acrylamide compounds having an amino group, such as N,N-dimethylaminoethyl(meth)acrylamide, N,N-diethylaminoethyl(meth)acrylamide, N,N-dipropylaminoethyl(meth)acrylamide, N,N-dibutylaminoethyl(meth)acrylamide, N,N-dimethylaminopropyl(meth)acrylamide, N,N-diethylaminopropyl(meth)acrylamide, N,N-dipropylaminopropyl(meth)acrylamide, N,N-dibutylaminopropyl(meth)acrylamide, N,N-dimethylaminobutyl(meth)acrylamide, N,N-diethylaminobutyl(meth)acrylamide, N,N-dipropylaminobutyl(meth)acrylamide, and N,N-dibutylaminobutyl(meth)acrylamide. These may be used alone, or two or more thereof may be used in combination. In view of improving the viscosity and curability of the resin composition for stereolithographic modeling, and providing a cured product having improved mechanical properties, the (meth)acrylamide compound (A-2) is more preferably N,N-dimethyl(meth)acrylamide, N,N-diethyl(meth)acrylamide, N-acryloylmorpholine, N,N-dimethylaminoethyl(meth)acrylamide, or N,N-diethylaminoethyl(meth)acrylamide, even more preferably N,N-diethyl(meth)acrylamide or N-acryloylmorpholine.

The content of (meth)acrylamide compound (A-2) in the resin composition for stereolithographic modeling of the present invention is preferably 1.0 to 60 mass %, more preferably 2.5 to 40 mass %, even more preferably 5 to 20 mass % in the total amount of the polymerizable monomer (A).

Polyfunctional (Meth)Acrylic Acid Ester Compound (A-3) Having a Viscosity of More Than 1,000 mPa·s In the resin composition for stereolithographic modeling of the present invention, the polyfunctional (meth)acrylic acid ester compound (A-3) having a viscosity of more than 1,000 mPa·s (hereinafter, also referred to simply as "polyfunctional (meth)acrylic acid ester compound (A-3)") is contained in the resin composition for stereolithographic modeling of the present invention to impart strength and toughness to a cured product of the resin composition for stereolithographic modeling.

Examples of the polyfunctional (meth)acrylic acid ester compound (A-3) include aromatic bifunctional (meth)acrylic acid ester compounds, aliphatic bifunctional (meth)acrylic acid ester compounds, and tri- and higher-functional (meth)acrylic acid ester compounds. The polyfunctional (meth)acrylic acid ester compound (A-3) may be used alone, or two or more thereof may be used in combination.

Examples of the aromatic difunctional (meth)acrylic acid ester compound include 2,2-bis((meth)acryloyloxyphenyl)propane, 2,2-bis[4-(3-acryloyloxy-2-hydroxypropoxy)phenyl]propane, 2,2-bis[4-(3-methacryloyloxy)-2-hydroxypropoxyphenyl]propane (commonly known as "Bis-GMA"), and 2,2-bis(4-(meth)acryloyloxyethoxyphenyl)propane.

Examples of the aliphatic difunctional (meth)acrylic acid ester compound include 1,2-bis(3-methacryloyloxy-2-hydroxypropoxy)ethane and 2,2,4-trimethylhexamethylene bis(2-carbamoyloxyethyl)dimethacrylate (commonly known as "UDMA"). In view of improving the curability and providing a cured product having desirable strength, the aliphatic difunctional (meth)acrylic acid ester compound is preferably 2,2,4-trimethylhexamethylene bis(2-carbamoyloxyethyl)dimethacrylate.

Examples of the tri- and higher-functional (meth)acrylic acid ester compound include dipentaerythritol penta(meth)acrylate, N,N-(2,2,4-trimethylhexamethylene)bis[2-(aminocarboxy)propane-1,3-diol]tetra(meth)acrylate, and 1,7-diacryloyloxy-2,2,6,6-tetra(meth)acryloyloxymethyl-4-oxaheptane.

The polyfunctional (meth)acrylic acid ester compound (A-3) of the present invention is preferably a polyfunctional (meth)acrylic acid ester compound having a urethane bond per molecule in view of obtaining a three-dimensional object having desirable toughness.

The polyfunctional (meth)acrylic acid ester compound having a urethane bond per molecule can be synthesized with ease through addition reaction of, for example, a polyol having any of later-described polymer skeletons, a compound having an isocyanate group (—NCO), and a (meth) acrylic compound having a hydroxyl group (—OH). Alternatively, the polyfunctional (meth)acrylic acid ester compound having a urethane bond per molecule can be synthesized with ease through ring-opening addition reaction of a (meth)acrylic compound having a hydroxyl group with a lactone or an alkylene oxide and then addition reaction of the resulting compound having a hydroxyl group at one terminal with a compound having an isocyanate group. The polyfunctional (meth)acrylic acid ester compound having a urethane bond per molecule may contain a ring structure in a polyol structure, but preferably contains no ring structure in a polyol structure. Examples of the ring structure include, as described for the (meth)acrylic acid ester compound (A-1), aromatic rings, alicyclic rings, and heterocycles.

The polyfunctional (meth)acrylic acid ester compound having a urethane bond per molecule preferably has a urethane bond and a structure (polymer skeleton) selected from the group consisting of a polyester, a polycarbonate, a polyurethane, a polyether, a poly(conjugated diene), and a hydrogenated poly(conjugated diene) in view of obtaining a three-dimensional object having desirable toughness. The polyfunctional (meth)acrylic acid ester compound having a urethane bond per molecule is not particularly limited as long as it has any of the above structures. Examples of the polyester include a polymer of a dicarboxylic acid (an aromatic dicarboxylic acid such as phthalic acid or isophthalic acid; or an unsaturated aliphatic dicarboxylic acid such as maleic acid) and an aliphatic diol having 2 to 18 carbon atoms, a polymer of a dicarboxylic acid (a saturated aliphatic dicarboxylic acid such as adipic acid or sebacic acid) and an aliphatic glycol having 2 to 18 carbon atoms, a β-propiolactone polymer, a γ-butyrolactone polymer, a δ-valerolactone polymer, an ε-caprolactone polymer, and copolymers thereof, and preferred are a polymer of a dicarboxylic acid (an aromatic dicarboxylic acid such as phthalic acid or isophthalic acid; or an unsaturated aliphatic dicarboxylic acid such as maleic acid) and an aliphatic diol having 2 to 12 carbon atoms and a polymer of a dicarboxylic acid (a saturated aliphatic dicarboxylic acid such as adipic acid or sebacic acid) and an aliphatic glycol having 2 to 12 carbon atoms. Examples of the polycarbonate include a polycarbonate derived from an aliphatic diol having 2 to 18 carbon atoms, a polycarbonate derived from bisphenol A, and a polycarbonate derived from an aliphatic diol having 2 to 18 carbon atoms and bisphenol A, and a polycarbonate derived from an aliphatic diol having 2 to 12 carbon atoms, a polycarbonate derived from bisphenol A, and a polycarbonate derived from an aliphatic diol having 2 to 12 carbon atoms and bisphenol A are preferred. Examples of the polyurethane include a polymer of an aliphatic diol having 2 to 18 carbon atoms and a diisocyanate having 1 to 18 carbon atoms, and a polymer of an aliphatic diol having 2 to 12 carbon atoms and a diisocyanate having 1 to 12 carbon atoms is preferred. Examples of the polyether include polyethylene glycol, polypropylene glycol, polybutylene glycol, and poly(1-methylbutyleneglycol). Examples of the poly(conjugated diene) and the hydrogenated poly(conjugated diene) include 1,4-polybutadiene, 1,2-polybutadiene, poly-isoprene, poly(butadiene-isoprene), poly(butadiene-styrene), poly(isoprene-styrene), polyfarnesene, and hydrogenated products of these. In view of improving the strength and toughness, structures of the polyesters and polycarbonates are preferred. A polyol having any of the above polymer skeletons can be used to produce the polyfunctional (meth) acrylic acid ester compound having a urethane bond per molecule.

Examples of the compound having an isocyanate group include hexamethylene diisocyanate (HDI), tolylene diisocyanate (TDI), xylylene diisocyanate (XDI), diphenylmethane diisocyanate (MDI), isophorone diisocyanate (IPDI), trimethylhexamethylene diisocyanate (TMHMDI), tricyclodecane diisocyanate (TCDDI), and adamantane diisocyanate (ADI).

Examples of the (meth)acrylic compound having a hydroxyl group include: hydroxy(meth)acrylate compounds such as 2-hydroxyethyl (meth)acrylate, 2-hydroxypropyl (meth)acrylate, 2-hydroxybutyl (meth)acrylate, 6-hydroxyhexyl (meth)acrylate, 10-hydroxydecyl (meth)acrylate, 3-chloro-2-hydroxypropyl (meth)acrylate, 2-hydroxy-3-phenoxypropyl (meth)acrylate, glycerin mono(meth)acrylate, 2-hydroxy-3-acryloyloxypropyl (meth)acrylate, 2,2-bis [4-[3-(meth)acryloyloxy-2-hydroxypropoxy]phenyl] propane, 1,2-bis[3-(meth)acryloyloxy-2-hydroxypropoxy] ethane, pentaerythritol tri(meth)acrylate, and dipentaerythritol tri(meth)acrylate or dipentaerythritol tetra (meth)acrylate; and hydroxy(meth)acrylamide compounds such as N-hydroxyethyl (meth)acrylamide and N,N-bis(2-hydroxyethyl) (meth)acrylamide.

The addition reaction between the compound having an isocyanate group and the (meth)acrylic compound having a hydroxyl group is not particularly limited, and may be carried out according to a known method.

The polyfunctional (meth)acrylic acid ester compound having a urethane bond per molecule produced by the reaction is, for example, a reaction production of any combination of the above polyol having a structure selected from the group consisting of the polyester, the polycarbonate, the polyurethane, the polyether, the poly(conjugated diene), and the hydrogenated poly(conjugated diene); the above compound having an isocyanate group; and a (meth) acrylic acid ester compound having a hydroxyl group.

In view of viscosity and strength, the weight-average molecular weight (Mw) of the polyfunctional (meth)acrylic acid ester compound (A-3) is preferably 400 to 50,000, more preferably 750 to 30,000, even more preferably 1,000 to 15,000, particularly preferably 1,100 to 10,000. The weight-average molecular weight (Mw) can be measured by a known method such as GPC analysis.

The content of the polyfunctional (meth)acrylic acid ester compound (A-3) in the resin composition for stereolithographic modeling of the present invention is preferably 20 to 99 mass % in the total amount of the polymerizable monomers. In view of improving fabricability and providing a cured product having improved strength and toughness, the content of the polyfunctional (meth)acrylic acid ester compound (A-3) is more preferably 30 to 95 mass %, even more preferably 40 to 90 mass %.

In the resin composition for stereolithographic modeling of the present invention, the (meth)acrylic acid ester compound (A-1), the (meth)acrylamide compound (A-2), and the polyfunctional (meth)acrylic acid ester compound (A-3) does not have an odor. It is preferable that the resin composition for stereolithographic modeling of the present invention is substantially free of an additional polymerizable monomer other than the (meth)acrylic acid ester compound (A-1), the (meth)acrylamide compound (A-2), and the polyfunctional (meth)acrylic acid ester compound (A-3). It is preferable that the resin composition for stereolithographic modeling of the present invention is substantially free of, for example, a polymerizable monomer (for example, a (meth)acrylic acid ester compound having a heterocycle, such as tetrahydrofurfuryl methacrylate) having an odor. Being substantially free of the additional polymerizable monomer means that the content of the additional polymerizable monomer is less than 1.0 mass % in the resin composition for stereolithographic modeling of the present invention. The content of the additional polymerizable monomer is preferably less than 0.1 mass %, more preferably less than 0.01 mass %.

Photopolymerization Initiator (B)

In view of improving the shape accuracy and providing a cured product having desirable strength, toughness, and color tone, the photopolymerization initiator (B) used in the present invention is at least one selected from a (bis)acylphosphine oxide, an α-hydroxyketone compound, an α-aminoketone compound, a benzoin alkyl ether compound, a thioxanthone, a ketal, an α-diketone, a coumarin, and an anthraquinone, and is preferably at least one selected from a (bis)acylphosphine oxide, an α-hydroxyketone compound, an α-aminoketone compound, a benzoin alkyl ether compound, a thioxanthone, a ketal, an α-diketone, and an anthraquinone.

More preferably, the photopolymerization initiator (B) is at least one selected from the group consisting of a (bis)acylphosphine oxide, an α-hydroxyketone compound, and an α-aminoketone compound because of strong absorption in the ultraviolet region and weak absorption at 450 nm or more in the visible region where colors can be easily perceived by the eye. In this case, the resin composition for stereolithographic modeling can be obtained that has desirable photocurability in the ultraviolet region, that shows sufficient photocurability even when the light source is a laser such as an Ar laser or a He—Cd laser or a lighting such as a halogen lamp, a xenon lamp, a metal halide lamp, a light-emitting diode (LED), a mercury lamp, or a fluorescent lamp, and that is resistant to coloring.

Examples of acylphosphine oxides in the (bis)acylphosphine oxide include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoylphenylphosphine oxide. Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Other examples include the compounds mentioned in JP 2000-159621 A.

Among these (bis)acylphosphine oxides, particularly preferred as photopolymerization initiator (B) are 2,4,6-trimethylbenzoyldiphenylphosphine oxide, 2,4,6-trimethylbenzoylmethoxyphenylphosphine oxide, and bis(2,4,6-trimethylbenzoyl)phenylphosphine oxide in view of improving the shape accuracy and providing a cured product having desirable color tone.

Examples of the α-hydroxyketone compound include 1-hydroxy-cyclohexyl phenyl ketone, 2-hydroxy-2-methyl-1-phenyl-1-propanone, and 2-hydroxy-1-[4-(2-hydroxyethoxy)phenyl]-2-methyl-1-propanone.

Examples of the α-aminoketone compound include 2-benzyl-2-(dimethylamino)-1-[(4-morpholino)phenyl]-1-butanone and 2-methyl-1-[4-(methylthio)phenyl]-2-(4-morpholinyl)-1-propanone.

Examples of the benzoin alkyl ether compound include benzoin methyl ether, benzoin ethyl ether, benzoin isopropyl ether, and benzoin isobutyl ether.

Examples of the thioxanthone that can be used include thioxanthone, 2-chlorothioxanthene-9-one, 2-hydroxy-3-(9-oxy-9H-thioxanthene-4-yloxy)-N,N,N-trimethyl-propaneaminium chloride, 2-hydroxy-3-(1-methyl-9-oxy-9H-thioxanthene-4-yloxy)-N,N,N-trimethyl-propaneaminium chloride, 2-hydroxy-3-(9-oxo-9H-thioxanthene-2-yloxy)-N,N,N-trimethyl-propaneaminium chloride, 2-hydroxy-3-(3,4-dimethyl-9-oxo-9H-thioxanthene-2-yloxy)-N,N,N-trimethyl-1-propaneaminium chloride, 2-hydroxy-3-(3,4-dimethyl-9H-thioxanthene-2-yloxy)-N, N, N-trimethyl-1-propaneaminium chloride, and 2-hydroxy-3-(1,3,4-trimethyl-9-oxo-9H-thioxanthene-2-yloxy)-N,N,N-trimethyl-1-propane aminium chloride.

Examples of the ketal include benzyl dimethyl ketal and benzyl diethyl ketal.

Examples of the α-diketone include diacetyl, benzyl, camphorquinone, 2,3-pentadione, 2,3-octadione, 9,10-phenanthrenequinone, 4,4'-oxybenzyl, and acenaphthenequinone. Examples of the coumarin include compounds described in JP H9(1997)-003109 A and JP H10(1998)-245525 A, such as 3,3'-carbonylbis(7-diethylaminocoumarin), 3-(4-methoxybenzoyl)coumarin, 3-benzoyl-7-methoxycoumarin, 3-benzoyl-6-methoxycoumarin, 3-benzoyl-8-methoxycoumarin, 3-(2-benzothiazolyl)-7-(dioctylamino)coumarin, 3-acetyl-7-(dimethylamino)coumarin, and 3,3'-carbonylbis(7-dibutylaminocoumarin).

Examples of the anthraquinone include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

The content of the photopolymerization initiator (B) in the resin composition for stereolithographic modeling of the present invention is not particularly limited, as long as the present invention can exhibit its effects. However, in view of curability, shape accuracy, and other properties of the resin composition for stereolithographic modeling, the content of the photopolymerization initiator (B) is preferably 0.01 to 10 parts by mass with respect to total 100 parts by mass of the polymerizable monomer (A). If the content of the photopolymerization initiator (B) is less than 0.01 parts by mass with respect to total 100 parts by mass of the polymerizable monomer (A), curing may not sufficiently proceed, resulting in a failure to obtain a three-dimensional object. The content of the photopolymerization initiator (B) is more preferably 0.1 parts by mass or more, even more preferably 0.5 parts by mass or more with respect to total 100 parts by mass of the polymerizable monomer (A). If the content of the photopolymerization initiator (B) is more than 10 parts by mass with respect to total 100 parts by mass of the polymerizable monomer (A) and the photopolymerization initiator itself has a low solubility, the photopolymerization initiator (B) may precipitate out of the resin composition for stereolithographic modeling and a cured product may discolor. The content of the photopolymerization initiator (B) is more preferably 7.5 parts by mass or less, even more preferably 5 parts by mass or less with respect to total 100 parts by mass of the polymerizable monomer.

It is preferred that the resin composition for stereolithographic modeling of the present invention is substantially free of a photopolymerization initiator other than the photopolymerization initiator (B). Examples of the other photopolymerization initiator include a metallocene compound. Examples of the metallocene compound include organic metal compounds having a cyclopentadienyl anion as an $\eta^5$-ligand. "Being substantially free of a photopolymerization initiator other than the photopolymerization initiator (B)" means that the content of the other photopolymerization initiator is less than 0.1 mass % in the resin composition for stereolithographic modeling of the present invention, and is preferably less than 0.01 mass %, more preferably less than 0.001 mass %.

Organic Peroxide (C)

The organic peroxide (C) used in the present invention is not particularly limited, and a known organic peroxide can be used. Examples of the organic peroxide (C) include ketone peroxides, hydroperoxides, diacyl peroxides, dialkyl peroxides, peroxyketals, peroxyesters, and peroxydicarbonates in view of producing no odor and providing a cured product having desirable strength, toughness, and color tone. In view of curability and storage stability, hydroperoxides and diacyl peroxides are preferably used.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide. Among these, cumene hydroperoxide, t-butyl hydroperoxide, and 1,1,3,3-tetramethylbutyl hydroperoxide are preferred.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide. Among these, benzoyl peroxide is preferred.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valeric acid.

Examples of the peroxyesters include α-cumylperoxy neodecanoate, t-butylperoxy neodecanoate, t-butyl peroxypivalate, 2,2,4-trimethylpentylperoxy-2-ethylhexanoate, t-amylperoxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleic acid.

Examples of the peroxydicarbonates include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

The content of the organic peroxide (C) used in the present invention is not particularly limited. However, in view of improving the strength and toughness of a cured product of the resin composition for stereolithographic modeling, the content of the organic peroxide (C) is preferably 0.001 to 10 parts by mass with respect to total 100 parts by mass of the polymerizable monomer (A). If the content of the organic peroxide (C) is less than 0.001 parts by mass with respect to total 100 parts by mass of the polymerizable monomer (A), polymerization may not sufficiently proceed, resulting in a failure to obtain sufficient strength and toughness of a cured product. The content of the organic peroxide (C) is more suitably 0.01 parts by mass or more, even more suitably 0.1 parts by mass or more. If the content of the organic peroxide (C) is more than 10 parts by mass with respect to total 100 parts by mass of the polymerizable monomer (A), the organic peroxide (C) may precipitate out of the resin composition and solidification may occur during storage. The content of the organic peroxide (C) is more suitably 5 parts by mass or less, even more suitably 2.5 parts by mass or less, and most suitably 1.0 parts by mass or less.

The resin composition for stereolithographic modeling of the present invention may further comprise a filler (D) to adjust paste properties or to alter the surface properties or strength of a cured product of the resin composition for stereolithographic modeling. Examples of the filler (D) include organic fillers, inorganic fillers, and organic-inorganic composite fillers. The filler (D) may be used alone, or two or more thereof may be used in combination.

Examples of the material of the organic filler include polymethyl methacrylate, polyethyl methacrylate, methyl methacrylate-ethyl methacrylate copolymer, crosslinked polymethyl methacrylate, crosslinked polyethyl methacrylate, polyesters, polyamides, polycarbonates, polyphenylene ethers, polyoxymethylene, polyvinyl chloride, polystyrene, polyethylene, polypropylene, chloroprene rubber, nitrile rubber, ethylene-vinyl acetate copolymer, styrene-butadiene copolymer, acrylonitrile-styrene copolymer, and acrylonitrile-styrene-butadiene copolymer. One of these may be used alone, or two or more thereof may be used in combination. The shape of the organic filler is not limited to a particular one, and the particle diameter of the filler can be selected as appropriate. In view of handling properties, mechanical strength, and other properties of the resulting resin composition for stereolithographic modeling, the average particle diameter of the organic filler is preferably 0.001 to 50 μm, more preferably 0.001 to 10 μm, even more preferably 0.001 to 1.0 μm.

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass-ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. One of these may be used alone, or two or more thereof may be used in combination. The shape of the inorganic filler is not limited to a particular one, and an irregularly-shaped filler or a spherical filler can be selected as appropriate. In view of handling properties, mechanical strength, and other properties of the resulting resin composition for stereolithographic modeling, the average particle diameter of the inorganic filler is preferably 0.001 to 50 μm, more preferably 0.001 to 10 μm, even more preferably 0.001 to 1.0 μm.

In order to adjust the flowability of the resin composition for stereolithographic modeling, the inorganic filler may be used after an optional surface treatment with a known surface treatment agent such as a silane coupling agent. Examples of the surface treatment agent include vinyltrimethoxysilane, vinyltriethoxysilane, vinyltrichlorosilane, vinyltri(β-methoxyethoxy)silane, γ-methacryloyloxypropyltrimethoxysilane, 8-methacryloyloxyoctyltrimethoxysilane, 11-methacryloyloxyundecyltrimethoxysilane, γ-glycidoxypropyltrimethoxysilane. γ-mercaptopropyltrimethoxysilane, and γ-aminopropyltriethoxysilane.

The organic-inorganic composite filler used in the present invention is a filler prepared by pulverizing a product of polymerization of a paste-like material prepared by adding a monomer component to the above inorganic filler. As the organic-inorganic composite filler, for example, a TMPT filler (a polymerized and pulverized mixture of trimethylolpropanetrimethacrylate and a silica filler) can be used. The shape of the organic-inorganic composite filler is not limited to a particular one, and the particle diameter of the filler can be selected as appropriate. In view of handling properties, mechanical strength, and other properties of the resulting resin composition for stereolithographic modeling, the average particle diameter of the organic-inorganic filler is preferably 0.001 to 50 µm, more preferably 0.001 to 10 µm, even more preferably 0.001 to 1.0 µm.

In the present specification, the average particle diameter of the filler is an average primary particle diameter, and can be determined by a laser diffraction scattering method or by electron microscope observation of the particles. Specifically, the laser diffraction scattering method is convenient for particle diameter measurement on particles with a diameter of 0.1 µm or more, and electron microscope observation is convenient for particle diameter measurement on ultrafine particles with a diameter of less than 0.1 µm. The particle diameter of 0.1 µm is a value determined by the laser diffraction scattering method.

To be specific about the laser diffraction scattering method, for example, the average particle diameter can be measured using a 0.2% aqueous solution of sodium hexametaphosphate as a dispersion medium by means of a laser diffraction particle size distribution analyzer (SALD-2300 manufactured by Shimadzu Corporation).

As a specific example of electron microscopy, particles may be photographed with an electron microscope (Model S-4000, manufactured by Hitachi, Ltd.), and the diameters of particles (at least 200 particles) observed in a unit field of the micrograph may be measured using image-analyzing particle-size-distribution measurement software (Macview, manufactured by Mountech Co., Ltd.). Here, the particle diameters are each determined as an arithmetic mean value of the maximum and minimum lengths of each particle, and the average primary particle diameter is calculated from the number of particles and their particle diameters.

The content of the filler (D) in the resin composition for stereolithographic modeling of the present invention is not particularly limited. However, in view of the viscosity, shape accuracy, and other properties of the resulting resin composition for stereolithographic modeling, the content of the filler (D) is preferably 400 parts by mass or less with respect to total 100 parts by mass of the polymerizable monomer (A). If the content of the filler (D) is more than 400 parts by mass with respect to total 100 parts by mass of the polymerizable monomer (A), the viscosity of the resin composition for stereolithographic modeling increases too much to fabricate an object. The content of the filler (D) is more preferably 200 parts by mass or less, even more preferably 100 parts by mass or less with respect to total 100 parts by mass of the polymerizable monomer (A).

The resin composition for stereolithographic modeling of the present invention may contain a polymerization accelerator to improve photocurability, provided that addition of a polymerization accelerator is not against the intent and purpose of the present invention. Examples of the polymerization accelerator include ethyl 4-(N,N-dimethylamino) benzoate, methyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino)benzophenone, and butyl 4-(N,N-dimethylamino)benzoate.

The resin composition for stereolithographic modeling of the present invention may comprise a polymer to alter properties such as flexibility and flowability, provided that addition of a polymer is not against the intent and purpose of the present invention. Examples of polymers that may be added in the present invention include natural rubber, synthetic polyisoprene rubber, liquid polyisoprene rubber, hydrogenated products of these, polybutadiene rubber, liquid polybutadiene rubber, hydrogenated products of these, styrene-butadiene rubber, chloroprene rubber, ethylene-propylene rubber, acryl rubber, isoprene-isobutylene rubber, acrylonitrile-butadiene rubber, and styrene elastomers. Specific examples of other polymers that may be added in the present invention include a polystyrene-polyisoprene-polystyrene block copolymer, a polystyrene-polybutadiene-polystyrene block copolymer, a poly(α-methylstyrene)-polybutadiene-poly(α-methylstyrene) block copolymer, a poly(p-methylstyrene)-polybutadiene-poly(p-methylstyrene) block copolymer, and hydrogenated products of these.

The resin composition for stereolithographic modeling of the present invention may optionally comprise a softener. Examples of the softener include petroleum-base softeners such as paraffinic, naphthenic, and aromatic process oils, and vegetable oil-base softeners such as paraffin, peanut oil, and rosin. These softeners may be used alone, or two or more thereof may be used in combination. The softener content is not particularly limited, provided that it is not against the intent and purpose of the present invention. Typically, the softener content is at most 200 parts by mass, preferably at most 100 parts by mass with respect to total 100 parts by mass of the polymerizable monomer (A).

The resin composition for stereolithographic modeling of the present invention may comprise a known stabilizer, in order to inhibit deterioration, or to adjust photocurability. Examples of such stabilizers include ultraviolet absorbers, polymerization inhibitors, and antioxidants.

Examples of the polymerization inhibitors include hydroquinone, hydroquinone monomethyl ether, dibutylhydroquinone, dibutylhydroquinone monomethyl ether, t-butyl catechol, 2-t-butyl-4,6-dimethylphenol, 2,6-di-t-butylphenol, and 3,5-di-t-butyl-4-hydroxytoluene. The content of polymerization inhibitor is preferably 0.001 to 5.0 parts by mass with respect to total 100 parts by mass of the polymerizable monomer (A).

The resin composition for stereolithographic modeling of the present invention may comprise a known additive, in order to adjust a color tone of a cured product or paste properties. Examples of such additives include pigments, dyes, organic solvents, and thickeners. The method for producing the resin composition for stereolithographic modeling of the present invention is not particularly limited, and the resin composition for stereolithographic modeling of the present invention can be obtained by adding given amounts of the components. The order of addition is not particularly limited. The components may be added all at once or may be added in two or more batches. If necessary, the components may be mixed or kneaded, or may be subjected to defoaming such as vacuum defoaming. The resin composition for stereolithographic modeling of the present invention can be, for example, charged in one container to obtain a one-pack type resin composition for stereolithographic modeling. If necessary, the resin composition for stereolithographic modeling of the present invention may be of one-pack type or of two-pack type.

The resin composition for stereolithographic modeling of the present invention emits a weak odor, has desirable shape accuracy, and has desirable strength, toughness, and color tone when used for stereolithographical fabrication. The resin composition for stereolithographic modeling of the present invention can also be used for stereolithographic fabrication by an inkjet method. Therefore, the resin composition for stereolithographic modeling of the present invention can be used in applications where such advantages can be exploited. The resin composition for stereolithographic modeling of the present invention can be used, for example, for production of a three-dimensional object by stereolithographic modeling; a dental material; production of various molded articles, such as film-shaped objects and moldings, produced by a technique such as flow casting or casting; a die for coating or vacuum molding, and is particularly optimal for a dental material.

Another embodiment of the present invention is a method for producing a three-dimensional object with any of the above resin compositions for stereolithographic modeling by stereolithographic modeling.

In stereolithographic modeling with the resin composition for stereolithographic modeling of the present invention, any known stereolithographic modeling method and device may be used. In the present invention, the light energy used to cure the resin is preferably an active energy beam. As used herein, "active energy beam" means an energy ray capable of curing a photocurable resin composition, and includes, for example, ultraviolet light, an electron beam, X-rays, radiant rays, and high-frequency waves. For example, the active energy beam may be ultraviolet light of 300 to 420 nm wavelengths. The light source of active energy beam may be, for example, a laser such as an Ar laser or a He—Cd laser; or a lighting such as a halogen lamp, a xenon lamp, a metal halide lamp, an LED, a mercury lamp, and a fluorescent lamp. Lasers are particularly preferred. When the light source is a laser, the fabrication time can be reduced by increasing the energy level, and a three-dimensional object of high shape accuracy can be obtained by taking advantage of the desirable convergence of a laser beam.

Stereolithographic modeling with the resin composition for stereolithographic modeling of the present invention may use any known method and any known stereolithography system, and the method and device are not particularly limited, as noted above. However, a typical example of a stereolithographic modeling method preferred for use in the present invention is a method that produces a three-dimensional object of the desired shape through a repeated procedure that includes a step of forming a cured layer by selectively applying an active energy beam to the resin composition for stereolithographic modeling to obtain a cured layer having a desired pattern, and a step of continuously forming another cured layer thereon by similarly applying an active energy beam to a newly supplied, uncured liquid resin composition for stereolithographic modeling. The resulting three-dimensional object may be used as it is, or may be used after improving mechanical properties, shape stability, or other properties by, for example, post-curing the product under applied light or heat.

A three-dimensional object obtained by stereolithographic modeling is not limited to a particular structure, shape, or size, and these may be decided according to use. Typical examples of areas to which the stereolithographic modeling of the present invention is applicable include production of various models and molds, including, for example, models for assessing external designs in a designing process; models for checking functions of components and parts; resin molds for making molds; base models for making dies; and direct molds for prototype dies. More specifically, the stereolithographic modeling of the present invention is applicable to, for example, production of models or work models for precision components and parts, electrical and electronic components, furniture, architectural structures, automobile parts, various containers and vessels, castings, dies, and base molds. In particular, by taking advantage of the superior mechanical properties of a cured product, the stereolithographic modeling of the present invention can be highly effectively used for dental prostheses including, for example, materials of crowns such as temporary crowns, bridges such as temporary crown bridges, denture bases, dental mouthpieces (splints, orthodontic aligners, retainers, and the like), and the like. The resin composition for stereolithographic modeling of the present invention is also suitable for mouthguards used for protection against external forces in sport activities.

The present invention encompasses embodiments obtainable by combining the above features in various manners within the technical scope of the present invention as long as the effect of the present invention can be obtained.

EXAMPLES

The following describes the present invention in greater detail by way of Examples. It should be noted, however, that the present invention is in no way limited by the following Examples, and various changes may be made by a person with ordinary skill in the art within the technical idea of the present invention.

Components used for resin compositions for stereolithographic modeling of Examples and Comparative Examples are listed below with the abbreviations.

Polymerizable Monomer (A)

(Meth)Acrylic Acid Ester Compound (A-1) Having a Viscosity of 1,000 mPa·s or Less and a Normal Boiling Point of 270° C. or More D2.6E: 2,2-Bis(4-methacryloyloxypolyethoxyphenyl)propane (the average addition number of moles of an ethoxy group: 2.6) (manufactured by SHIN-NAKAMURA CHEMICAL Co., Ltd.) (viscosity at 25° C.: 950 mPa·s; atmospheric equivalent boiling point: 300° C. or more)

DPM: Dicyclopentanyl methacrylate (manufactured by Hitachi Chemical Company, Ltd.) (viscosity at 25° C.: 10 mPa·s; atmospheric equivalent boiling point: 285° C.)

(Meth)Acrylamide Compound (A-2) Having a Viscosity of 1,000 mPa·s or Less and a Normal Boiling Point of 200° C. or More ACMO: N-Acryloylmorpholine (manufactured by KJ CHEMICALS CORPORATION) (viscosity at 25° C.: 12 mPa·s; atmospheric equivalent boiling point: 255° C.)

Polyfunctional (Meth)Acrylic Acid Ester Compound (A-3) Having a Viscosity of More Than 1,000 mPa·s (A-3)-1 UDMA: 2,2,4-Trimethylhexamethylene bis(2-carbamoyloxyethyl)dimethacrylate (manufactured by SHIN-NAKAMURA CHEMICAL Co., Ltd.) (viscosity at 25° C.: 28,000 mPa·s)

Synthesis Example 1

Production of Polyfunctional (Meth)Acrylic Acid Ester Compound (A-3)-2

(1) First, 250 g of isophorone diisocyanate and 0.15 g of di-n-butyltin dilaurate were added into a 5 L four-neck flask equipped with a stirrer, a thermostat, a thermometer, and a condenser, and the mixture was heated to 70° C. while being stirred.

(2) Separately, 1,000 g of a polycarbonate polyol (Kuraray Polyol® C-1090 manufactured by Kuraray Co., Ltd.; a polyol with a 1,6-hexanediol:3-methyl-1,5-pentanediol mass ratio of 9:1; a weight-average molecular weight Mw of 1,000) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow for reaction.

(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a polyfunctional (meth)acrylic acid ester compound (A-3)-2. By GPC analysis, the weight-average molecular weight Mw of the polyfunctional (meth)acrylic acid ester compound (A-3)-2 was found to be 1,700.

Synthesis Example 2

Production of Polyfunctional (Meth)Acrylic Acid Ester Compound (A-3)-3

(1) First, 250 g of isophorone diisocyanate and 0.15 g of di-n-butyltin dilaurate were added into a 5 L four-neck flask equipped with a stirrer, a thermostat, a thermometer, and a condenser, and the mixture was heated to 70° C. while being stirred.

(2) Separately, 2,500 g of a polyester polyol (Kuraray Polyol® P-2050 manufactured by Kuraray Co., Ltd.; a polymeric diol of sebacic acid and 3-methyl-1,5-pentanediol; a weight-average molecular weight Mw of 2,000) was added into a dropping funnel equipped with a side tube, and the solution in the dropping funnel was dropped into the flask of (1). Here, the solution was dropped at a constant rate over a time period of 4 hours with the temperature inside the flask held at 65 to 75° C. while stirring the solution in the flask of (1). After dropping, the mixture was stirred at the same temperature for 2 hours to allow for reaction.

(3) Thereafter, a homogenous solution prepared by adding 150 g of 2-hydroxyethyl acrylate and 0.4 g of hydroquinone monomethyl ether into a different dropping funnel was dropped at a constant rate over a time period of 2 hours with the temperature inside the flask held at 55 to 65° C., and a reaction was allowed for 4 hours at the maintained solution temperature of 70 to 80° C. in the flask to obtain a polyfunctional (meth)acrylic acid ester compound (A-3)-3. By GPC analysis, the weight-average molecular weight Mw of the polyfunctional (meth)acrylic acid ester compound (A-3)-3 was found to be 2,600.

Photopolymerization Initiator (B)
TPO: 2,4,6-Trimethylbenzoyl diphenylphosphine oxide
BAPO: Bis(2,4,6-trimethylbenzoyl)phenylphosphine oxide
Organic Peroxide (C)
THP: 1,1,3,3-Tetramethylbutyl hydroperoxide (manufactured by NOF CORPORATION)
BPO: Benzoyl peroxide (manufactured by NOF CORPORATION)
Filler (D)
(D)-1: Dimethyldichlorosilane-surface-treated colloidal silica powder (R972 manufactured by Nippon Aerosil Co., Ltd.; average particle diameter: 0.016 μm)
Polymerization Inhibitor
BHT: 3,5-di-t-Butyl-4-hydroxytoluene Examples 1 to 8 and Comparative Examples 1 to 3

The components were mixed under ordinary temperature (20° C.±15° C., JIS Z 8703: 1983) in the amounts shown in Tables 1 and 2 to prepare pastes as resin compositions for stereolithographic modeling of Examples 1 to 8 and Comparative Examples 1 to 3.

Fabricability

A rectangular object measuring 64 mm in length, 10.0 mm in width, and 3.3 mm in thickness was produced using a stereolithography device (Digital Wax® 028J-Plus manufactured by DWS) from each of the compositions of Examples and Comparative Examples in Tables 1 and 2. The obtained object was washed with methanol to remove unpolymerized monomers and was then measured for dimensions (unit: mm) using a micrometer. A shape error was calculated using the following formula, and the shape accuracy was evaluated (n=1). When the shape error calculated thereby is 5.0% or less, the shape accuracy is desirable and a dental prosthesis, such as a crown, fabricated from the composition tends to have desirable conformity.

$$\text{Shape error (\%)} = \frac{(|(\text{Measured dimensions}) - 10.0|)}{10.0} \times 100$$

Strength (Flexural Modulus and Flexural Strength) and Toughness (Displacement of Fracture Point)

A rectangular object measuring 3.3 mm in thickness, 10.0 mm in width, and 64 mm in length was produced using a stereolithography device (DigitalWax® 028J-Plus manufactured by DWS; wavelength: 405 nm) from each of the resin compositions for stereolithographic modeling of Examples and Comparative Examples in Tables 1 and 2. The obtained object was washed with methanol to remove unpolymerized monomers and was then subjected to light irradiation for five minutes using an LED-curing unit (a light V manufactured by J. MORITA TOKYO MFG. CORP.; wavelength: 400 to 420 nm) for dental technique. Subsequently, the object was heated at 110° C. for 10 minutes using a dental heat curing unit (KL-400 manufactured by KURARAY NORITAKE DENTAL INC.). The resulting cured product was used as a specimen (64.0 mm in length, 10.0 mm in width, 3.3 mm in thickness) having dimensions described in JIS T 6501: 2012 (Acrylic Resin for Denture Base) in a flexural strength test to evaluate the cured product. The flexural test was conducted in accordance with JIS T 6501: 2012 using a universal testing machine (Autograph AG-I, 100 kN, manufactured by Shimadzu Corporation) at a crosshead speed of 5 mm/min (n=5). The flexural strength and flexural modulus of the cured product were found by calculating means from values measured for each specimen. The preferred range of the flexural moduli of the specimens is 0.1 to 5.0 GPa, more preferably 0.5 to 4.0 GPa, even more preferably 1.0 to 3.0 GPa in view of using as temporary crowns, temporary crown bridges, denture bases, dental mouthpieces, etc. which are dental prostheses. The preferred range of the flexural strengths of the specimens is 30 MPa or more, more preferably 40 MPa or more, even more preferably 50 MPa or more in view of using as temporary crowns, temporary crown bridges, denture bases, dental mouthpieces, etc. which are dental prostheses. As for the displacement of fracture point, it is preferred that each specimen does not fracture when a load equal to or higher than the above flexural strength is applied thereto. The toughness of a specimen was rated as poor when the specimen fractured at a displacement of 10 mm or less. The toughness of a specimen was rated as good when the specimen fractured at a displacement of more than 10 mm and less than 15 mm, and very good when the specimen fractured at a displacement of 15 mm or more. In Tables 1 and 2, "15<" means that the displacement was 15 mm or more and a specimen did not fracture at a displacement of 15 mm.

Odor

For the resin compositions for stereolithographic modeling of Examples and Comparative Examples, "Satisfactory" was given when one of 10 panelists smelled an unpleasant odor, "Acceptable" was given when two to four panelists smelled an unpleasant odor, and "Unsatisfactory" was given when five or more panelists smelled an unpleasant odor (n=1). The resin compositions are of satisfactory quality when there is no perceivable unpleasant odor.

Color Tone

A disc-shaped object measuring 15.0 mm in diameter and 1.0 mm in thickness was produced using a stereolithography device as described above from each of the resin compositions for stereolithographic modeling of Examples and Comparative Examples. The obtained object was washed with methanol to remove unpolymerized monomers and was then further subjected to secondary polymerization for five minutes using an LED-curing unit (a light V manufactured by J. MORITA TOKYO MFG. CORP.) for dental technique, followed by heating at 110° C. for 10 minutes using a heat curing unit (KL-400 manufactured by KURARAY NORITAKE DENTAL INC.) to obtain a cured product. The obtained cured product was ground with #1000 silicon carbide paper and then ground with a dental wrapping film (manufactured by 3M). After that, a yellowness index, a b* value, was measured using a spectrocolorimeter (CM-3610A manufactured by KONICA MINOLTA, INC.; compliant with the condition c in JIS Z 8722: 2009; illuminant D65), and a mean thereof was obtained (n=5). When the yellowness index of a cured product is 10.0 or less, the eye tends to perceive the cured product as colorless. The yellowness index is preferably 7.0 or less, more preferably 5.0 or less.

TABLE 1

| | | Example | | | | | | | |
|---|---|---|---|---|---|---|---|---|---|
| (Parts by mass) | | 1 | 2 | 3 | 4 | 5 | 6 | 7 | 8 |
| (A-1) | D2.6E | 70 | | | | | | | |
| | DPM | | 30 | 50 | 50 | | 50 | 30 | 50 |
| (A-2) | ACMO | | | | | 50 | | | |
| (A-3) | (A-3)-1 UDMA | | 70 | | | | | | |
| | (A-3)-2 | | | 50 | | | | | |
| | (A-3)-3 | | | | 50 | 50 | 50 | 70 | 50 |
| (B) | TPO | 3.0 | 3.0 | 4.0 | 4.0 | 4.0 | 2.0 | 4.0 | 4.0 |
| | BAPO | | | | | | 0.5 | | |
| (C) | THP | 0.1 | 0.1 | 0.2 | 0.2 | 0.2 | | 0.2 | 0.1 |
| | BPO | | | | | | 0.1 | | 0.05 |
| (D) | (D)-1 | | | | | | | | 10 |
| | BHT | 0.1 | 0.1 | 0.1 | 0.1 | 0.1 | 0.1 | 0.1 | 0.1 |
| Fabricability | | 4.5 | 3.8 | 3.4 | 3.0 | 3.1 | 3.6 | 3.8 | 4.8 |
| Strength, toughness | Flexural modulus (GPa) | 2.8 | 2.5 | 2.3 | 2.0 | 2.2 | 2.1 | 1.8 | 2.5 |
| | Flexural strength (MPa) | 85 | 90 | 70 | 65 | 60 | 62 | 55 | 80 |
| | Displacement of fracture point | 12 | 14 | 15< | 15< | 15< | 15< | 15< | 12 |
| Odor | | Satisfactory | Satisfactory | Satisfactory | Satisfactory | Satisfactory | Satisfactory | Satisfactory | Satisfactory |
| Color tone | Yellowness index (b* value) | 6.4 | 3.6 | 4.0 | 4.2 | 4.8 | 3.9 | 3.7 | 4.0 |

| | | Comparative Example | | |
|---|---|---|---|---|
| (Parts by mass) | | 1 | 2 | 3 |
| (A-1) | DPM | 50 | | 50 |
| (A-3) | (A-3)-2 | 50 | 50 | 50 |
| (A) | Tetrahydrofurfuryl methacrylate | | 50 | |
| (B) | TPO | 4.0 | 4.0 | |
| | Irgacure 784 (metallocene compound) | | | 4.0 |

-continued

|  | (Parts by mass) | Comparative Example | | |
|---|---|---|---|---|
|  |  | 1 | 2 | 3 |
| (C) | THP |  | 0.2 | 0.2 |
|  | BHT | 0.1 | 0.1 | 0.1 |
|  | Fabricability | 3.4 | 12 | 18 |
| Strength, | Flexural modulus (GPa) | 0.8 | 0.4 | 0.6 |
| toughness | Flexural strength (MPa) | 27 | 24 | 28 |
|  | Displacement of fracture point | 15< | 4.5 | 3.8 |
|  | Odor | Satisfactory | Unsatisfactory | Satisfactory |
| Color tone | Yellowness index (b* value) | 12.1 | 4.7 | 13.5 |

As shown in Tables 1 and 2, the resin compositions for stereolithographic modeling of Examples 1 to 8 had desirable fabricability, and the odor was weak. Strength and toughness were also desirable in the cured products of the resin compositions of Examples 1 to 8. Specifically, the cured products of the resin compositions for stereolithographic modeling of Examples 1 to 8 had more desirable strength and toughness than the cured products of the resin compositions of Comparative Examples 1 to 3. The resin compositions for stereolithographic modeling of Examples 1 to 8 had more desirable fabricability than the resin compositions of Comparative Examples 2 and 3. The cured products of the resin compositions for stereolithographic modeling of Examples 1 to 8 had more desirable color tones than the cured products of the resin compositions of Comparative Examples 1 and 3.

INDUSTRIAL APPLICABILITY

The resin composition for stereolithographic modeling of the present invention emits a weak odor when used for fabrication of an object, and has desirable shape accuracy and is made into a cured product having desirable mechanical properties and color tone when used for shaping by stereolithographic modeling. The resin composition for stereolithographic modeling of the present invention is therefore particularly suited for a dental material.

The invention claimed is:

1. A resin composition for stereolithographic modeling, comprising:
    a polymerizable monomer;
    a photopolymerization initiator; and
    an organic peroxide,
    wherein the polymerizable monomer comprises:
    a (meth)acrylic acid ester compound having a viscosity of 1,000 mPa·s or less and a normal boiling point of 270° C. or more, and/or
    a (meth)acrylamide compound having a viscosity of 1,000 mPa·s or less and a normal boiling point of 200° C. or more, and
    wherein
    the (meth)acrylic acid ester compound comprises a monofunctional (meth)acrylic acid ester compound having an aromatic ring and/or a monofunctional (meth)acrylic acid ester compound having an alicyclic ring, and
    the photopolymerization initiator is at least one selected from the group consisting of (bis)acylphosphine oxide, an α-hydroxyketone compound, an α-aminoketone compound, a benzoin alkyl ether compound, a thioxanthone, a ketal, an α-diketone, and an anthraquinone.

2. The resin composition for stereolithographic modeling according to claim 1, wherein the polymerizable monomer further comprises a polyfunctional (meth)acrylic acid ester compound having a viscosity of more than 1,000 mPa·s.

3. The resin composition for stereolithographic modeling according to claim 2, wherein the polyfunctional (meth)acrylic acid ester compound has a urethane bond per each molecule.

4. The resin composition for stereolithographic modeling according to claim 3, wherein the polyfunctional (meth)acrylic acid ester compound has at least one structure selected from the group consisting of a polyester, a polycarbonate, a polyurethane, a polyether, a poly(conjugated diene), and a hydrogenated poly(conjugated diene).

5. The resin composition for stereolithographic modeling according to claim 1, wherein the organic peroxide is at least one selected from the group consisting of a ketone peroxide, a hydroperoxide, a diacyl peroxide, a dialkyl peroxide, a peroxyketal, a peroxyester, and a peroxydicarbonate.

6. The resin composition for stereolithographic modeling according to claim 1,
    wherein the polymerizable monomer comprises the (meth)acrylic acid ester compound having a viscosity of 1,000 mPa·s or less and a normal boiling point of 270° C. or more.

7. The resin composition for stereolithographic modeling according to claim 1, wherein the (meth)acrylic acid ester compound comprises a monofunctional (meth)acrylic acid ester compound having an alicyclic ring.

8. The resin composition for stereolithographic modeling according to claim 7, wherein the monofunctional (meth)acrylic acid ester compound having an alicyclic ring is a monofunctional (meth)acrylic acid ester compound having a polyalicyclic ring.

9. The resin composition for stereolithographic modeling according to claim 1, further comprising a filler.

10. The resin composition for stereolithographic modeling according to claim 9, wherein an average primary particle diameter of the filler is 1.0 μm or less.

11. A dental material comprising a cured product of the resin composition for stereolithographic modeling according to claim 1.

12. A method for producing a three-dimensional object with the resin composition for stereolithographic modeling according to claim 1 by stereolithographic modeling, the method comprising:
    exposing the resin composition to light energy.

* * * * *